United States Patent

Tanaka et al.

[11] Patent Number: 5,037,740
[45] Date of Patent: Aug. 6, 1991

[54] NOVEL IMMOBILIZED CELLS AND FERMENTATION METHOD UTILIZING THE SAME

[75] Inventors: Hideo Tanaka, Niiharigu; Hiroshi Kurosawa, Hitachi; Mizuo Yajima, Tokyo, all of Japan

[73] Assignee: Asama Chemical Co., Ltd., Tokyo, Japan

[21] Appl. No.: 748,597

[22] Filed: Jun. 25, 1985

[51] Int. Cl.$^5$ .................. C12P 39/00; C12P 7/14; C12N 11/04
[52] U.S. Cl. .................. 435/42; 435/162; 435/161; 435/174; 435/176; 435/177; 435/182
[58] Field of Search ........... 435/161, 42, 139, 162, 435/182, 176, 177

[56] References Cited

FOREIGN PATENT DOCUMENTS 0212979 8/1984 Fed. Rep. of Germany.
2055121 2/1981 United Kingdom ............... 435/161
2113248 8/1983 United Kingdom ............... 435/161

Primary Examiner—Elizabeth C. Weimar
Assistant Examiner—Gail Paulos
Attorney, Agent, or Firm—Birch, Stewart, Kolasch & Birch

[57] ABSTRACT

Novel immobilized cells are prepared by immobilizing cells of at least one aerobic microorganism and cells of at least one anaerobic microorganism in a single gel immobilizing carrier. The immobilized cells are utilized in a fermentation method. Many useful fermentation products can be readily and economically obtained by using the immobilized cells which accommodate both aerobic and anaerobic metabolic function simultaneously.

19 Claims, 1 Drawing Sheet

Process of ethyl alcohol production from starch by immobilized cell mixture of Aspergillus awamori and Zymomonas mobilus Process of ethyl alcohol production from starch by immobilized cell mixture of Aspergillus awamori and Zymomonas mobilus

NOVEL IMMOBILIZED CELLS AND FERMENTATION METHOD UTILIZING THE SAME

BACKGROUND OF THE INVENTION

1. Field of the Invention

This invention relates to immobilized cells and a fermentation method utilizing the same. More particularly it relates to immobilized cells prepared by immobilizing aerobic and anaerobic cells in a single immobilizing carrier as well as to a fermentation method utilizing the same, wherein aerobic and anaerobic metabolic sequences are simultaneously carried out to thereby produce a fermentation product.

It is an object of the present invention to economically produce a fermentation product by preparing a carrier which accommodates both aerobic and anaerobic metabolic functions simultaneously and efficiently utilizes these functions.

2. Description of the Prior Art

Martin et al. have reported a fermentation method wherein cells of two microbial strains are simultaneously immobilized by a single carrier (C.K.A. Martin and D. Perlman, European J. Appl. Microbiol., 3, 91 (1976)). However both of these strains are aerobic and there has been no report relating to a fermentation method wherein a combination of aerobic and anaerobic cells is utilized.

Most of the studies on fermentation through the use of microbial cells and processes for industrial production utilizing microbial cells have been carried out by means of so-called pure cultures wherein a single strain is used. Recently demands have arisen for processes for conducting a series of fermentation operations through the use of two or more strains to thereby widen the range of materials to be fermented as well as fermentation products, and to achieve an economic advantage. These demands have led to a development of a so-called mixed culture wherein two or more strains are cultured in a single apparatus, unlike a conventional pure culture wherein the fermentation is carried out by using the same number of culture apparatuses as there are of strains. Although many attempts therefor have been conducted, most of these attempts have been unsuccessful. One principal reason therefor is that in a single culture apparatus wherein each of the ambient factors, such as pH value, temperature or medium composition, should be fixed uniquely, two strains whose optimum culture conditions are not always similar to each other can coexist only in a highly limited range. Even if appropriate conditions can be determined by supposing the coexistence of these cells, they are frequently undesirable for fermentation of either of the two strains. A second principal reason therefor is that when the optimum ambient conditions of two or more strains are identical by chance, these strains compete with each other for medium constituents and, additionally, for oxygen when both strains are aerobic. As a result, these strains are liable to separate into superior and inferior groups, which makes well-balanced coexistence of all cells difficult. When a combination of an aerobic strain requiring oxygen and an anaerobic strain not requiring oxygen is used in a series of fermentation operations, at least the competition between these strains with respect to oxygen can be avoided. Thus, attention need only be paid to the competition between them with respect to medium constituents, which considerably simplifies the setting of culture conditions. However, it is impossible in conventional liquid culture methods to set culture conditions which can simultaneously meet both the oxygen demand and lack thereof in a single culture apparatus. Accordingly, it is generally necessary to employ two culture apparatuses, one of which is set to aerobic conditions and the other of which is set to anaerobic conditions.

SUMMARY OF THE INVENTION

In view of preparing a culture of immobilized cells, we have carried out an experiment which comprises mixing aerobic and anaerobic microbial cells in an aqueous solution of a starting material so as to prepare an immobilizing carrier, causing the gelation of the obtained mixture to thereby prepare immobilized cell mixtures, introducing the cell mixtures into a nutritional medium and culturing the cell mixtures under aerobic conditions. Consequently, we have found that the aerobic cells would mainly grow on and near an oxygen-rich surface of the gel carrier, while the anaerobic cells would mainly grow at an oxygendeficient central part of the carrier. That is, these cells would spontaneously exhibit "habitat segregation" in the gel carrier. We have also found that the anaerobic microbial cells present inside the gel carrier would further metabolize the metabolites produced by the aerobic microbial cells on or near the surface of the carrier. Thus, such immobilized cell mixtures make it possible to simultaneously culture aerobic and anaerobic cells in a single culture apparatus under aerobic conditions.

We have further studied the establishment of novel immobilized cells and a fermentation method utilizing these cell. By taking advantage of the habitat segregation as described above, we have thus completed the present invention.

DETAILED DESCRIPTION OF THE INVENTION

Figure 1:
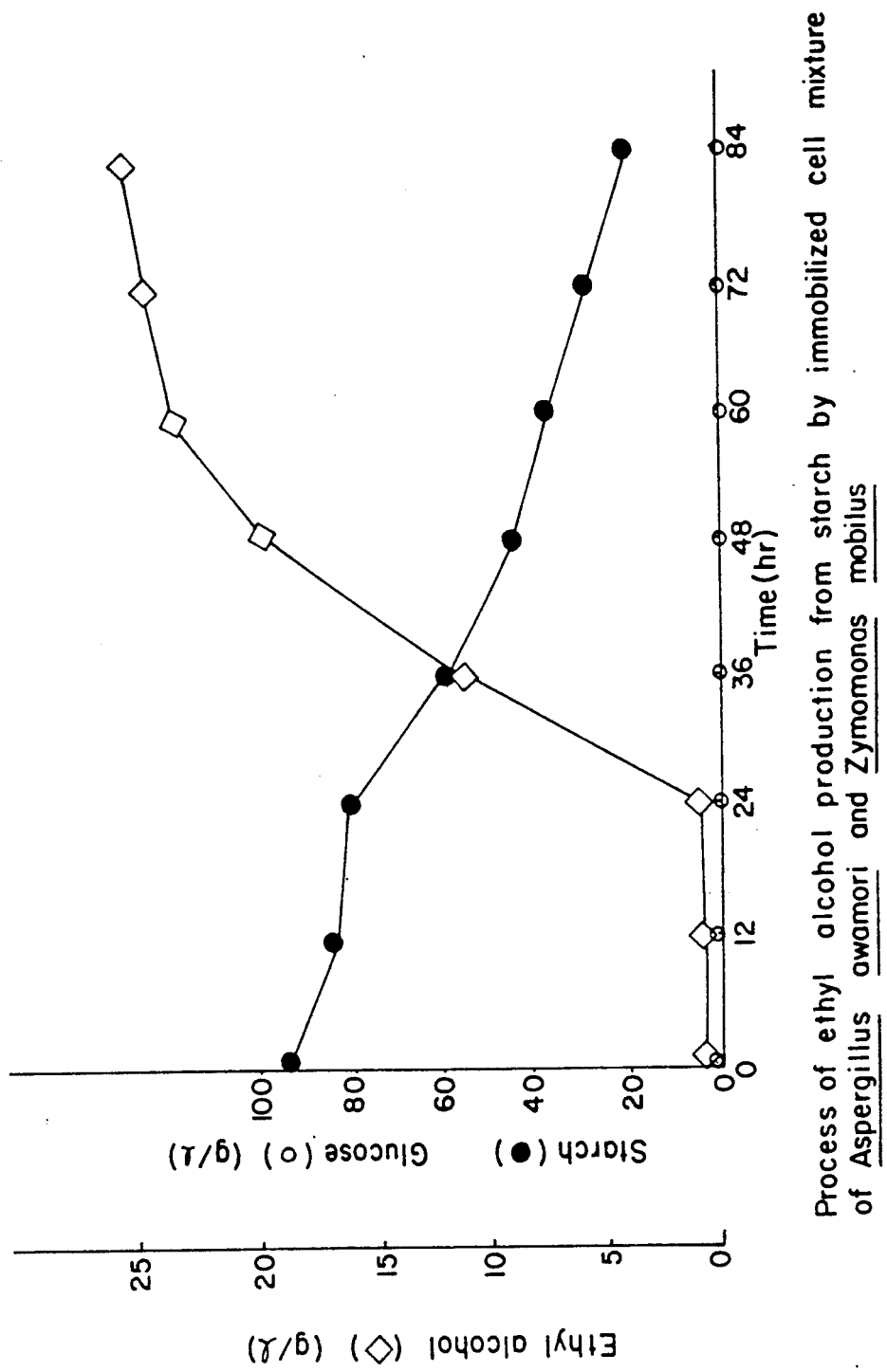

The aerobic microbial cells which can be used in the present invention are not particularly limited and include any cells such as fungi, yeast, actinomycetes and bacteria. Similarly any anaerobic cells such as yeasts and bacteria may be employed in the present invention. These cells are readily available. Immobilized cells comprising two or more strains in a gel carrier may be prepared by mixing cells of at least one aerobic strain, cells of at least one anaerobic strain, i.e. at least two in total, and an aqueous solution containing a starting material for an immobilizing carrier, such as an alginate, and converting the carrier into a waterinsoluble salt thereof in a conventional manner. The mixed cells immobilized by the gel carrier thus obtained may be cultured under aerobic conditions in a medium selected to allow the coexistence of these cells. Thus, an immobilized cell mixture, wherein the aerobic cells grow on and near the surface of the gel carrier while the anaerobic cells grow at the central part thereof, can be prepared to thereby efficiently metabolize the substrates and metabolites. The immobilized cells thus prepared exhibit various remarkable advantages from an economical viewpoint. That is, fermentation products, which have been conventionally produced by separately using aerobic and anaerobic microorganisms with the use of two or more culture apparatuses in two steps, can be produced in a single step and in a single culture apparatus under aerobic conditions by utilizing the immobilized cells. Furthermore, these immobilized cells can be used repeatedly since they can be cultured in an existing apparatus and readily separated from the medium.

Any conventional materials capable of forming a gel may be used in preparing said immobilized cells.

For example, natural materials such as alginates, κ-carrageenan, agar, collagen and gelatin and synthetic materials such as polyacrylamide, photocrosslinked resin prepolymers and urethane polymers may be employed. Among the nutrients required by the cells to be immobilized, those which are expensive and required in a small amount, such as vitamins or amino acids, may be simultaneously immobilized in the immobilizing carrier so that they can be supplied in a small amount at a high concentration to the microorganisms without adding a large amount thereof to the medium.

Any fermentation products obtained by combining aerobic and anaerobic microbial cells, such as ethyl alcohol, lactic acid, acetone or butanol, can be produced by a fermentation method utilizing the immobilized cells of the present invention.

To further illustrate the present invention, the following examples are given.

EXAMPLE 1

Production of ethyl alcohol from starch $10^8$ spores of *Aspergillus awamori* Nakazawa (IFO 4033), which is an aerobic microorganism, and 10 to 80 mg (on a dry basis) of *Zymomonas mobilus* (IFO 13756), which is an -anaerobic microorganism, obtained by stationarily culturing for 16 hours were added to 100 ml of a sterilized 3% aqueous solution of sodium alginate are thoroughly mixed therewith. The obtained mixture was added dropwise through a nozzle to a solution of calcium chloride to thereby form spherical immobilized cell mixtures diameter approximately 3 mm). 30 ml of the immobilized cell mixtures thus obtained were added to 200 ml of a starch medium containing 2% of soluble starch, 0.5% of peptone, 0.2% of yeast extract, 0.5% of $KH_2PO$, 0.1% of $MgSO_4 \cdot 7H_2O$, 0.001% of $FeSO_4 \cdot 7H_2O$ and 0.5% of $CaCl_2$ (pH 5.5) and cultured therein in an Erlenmeyer flask of 500 ml in volume at 100 rpm and at 30° C. Table 1 shows the fermentative production of ethyl alcohol from starch after culturing for 48 hours. The ethyl alcohol was determined by gas chromatography.

TABLE 1

Production of ethyl alcohol from starch by immobilized cell mixture of *Aspergillus awamori*\* and *Zymomonas mobilus*

| *Zymomonas mobilus* Inoculated (mg on a dry basis) | Produced alcohol (g/l) | Yield with respect to starch (%) |
| --- | --- | --- |
| 0 | 0 | 0 |
| 10 | 3.5 | 21.2 |
| 20 | 5.4 | 32.7 |
| 30 | 7.0 | 42.5 |
| 40 | 5.2 | 31.5 |
| 80 | 4.5 | 27.2 |

\*$10^8$ spores of *Aspergillus awamori* were inoculated in each case.

Table 1 indicates that *Aspergillus awamori* alone can not produce ethyl alcohol from starch. When $10^8$ spores of *Aspergillus awamori* were inoculated, a maximum amount of ethyl alcohol can be produced by simultaneously inoculating 30 mg (on a dry basis) of *Zymomonas mobilus*. The yield with respect to starch content in this case is approximately similar to the maximum yield of ethyl alcohol obtained from the fermentation of glucose by immobilized *Zymomonas mobilus* alone. FIG. 1 shows the process of the fermentative production of ethyl alcohol when the concentration of starch is elevated to 9%. $10^8$ spores of *Aspergillus awamori* and 20 mg (on a dry basis) of *Zymomonas mobilus* were inoculated. The culture was carried out under the same condition as described above but rotating an Erlenmeyer flask of 500 ml in volume at 220 rpm to thereby supply an increased amount of oxygen.

FIG. 1 indicates that 27 g/l of ethyl alcohol is obtained as a yield with respect to a starch content of approximately 40% by culturing for 84 hours without any accumulation of glucose, which is an intermediate metabolite, in the medium during the fermentation period.

EXAMPLE 2

Production of lactic acid from starch $10^8$ spores of *Aspergillus niger*, which is an aerobic microorganism, and 50 mg (on a dry basis) of cells of *Streptococcus lactis*, which is an anaerobic microgranism obtained by a stationary culture, were added to a sterilized 3% aqueous solution of K-carrageenan and thoroughly mixed therewith. The obtained mixture was kept at 35° C. Then the mixture was added dropwise through a nozzle of approximately 1 mm in diameter to a 2% solution of potassium chloride to form sperical immobilized cell mixtures (diameter 3 mm). 30 ml of the mixtures thus prepared were added to a starch medium which comprised 2.5% of soluble starch, 0.5% of yeast extract, 0.5% of trypton, 0.1% of casamino acids, 0.25% of $K_2HPO_4$, 0.25% of $KH_2PO$ and 0.05% of $MgSO_4 \cdot 7H_2O$ (pH 5.5) and cultured therein in an Erlenmeyer flask of 500 ml in volume at 100 rpm and at 30° C. while controlling the pH value to 5.5 with sodium hydroxide.

The produced lactic acid was determined by using a lactic dehydrogenase kit (mfd. by Boehringer Co., Ltd.). As a result, 15 g/l of lactic acid was produced by culturing for 48 hours with little accumulation of glucose, which is an intermediate metabolite, in the medium.

What is claimed is:

1. A spherical immobilized cell mixture which comprises: cells of at least one aerobic microorganism located near the surface of said spherical cell mixture; cells of at least one anaerobic microorganism located in a central part of said spherical cell mixture; and an immobilizing carrier.

2. An immobilized cell mixture as set forth in claim 1, wherein said immobilizing carrier is a gel.

3. A method for producing a fermentation product which comprises immobilizing cells of at least one aerobic microorganism and cells of at least one anaerobic microorganism in an immobilizing carrier to produce spherical immobilized cell mixtures, and culturing said immobilized cell mixtures to produce a fermentation product.

4. A method for preparing spherical immobilized cell mixtures which comprises mixing cells of at least one aerobic microorganism, cells of at least one anaerobic microorganism and a solution of a substance capable of forming a gel, and subsequently causing gelation of this mixture to form said spherical immobilized cell mixtures.

5. An immobilized cell mixture as set forth in claim 1, wherein the aerobic microorganism is fungi, yeast, actinomycetes or bacteria.

6. An immobilized cell mixture as set forth in claim 1, wherein the anaerobic microorganism is a yeast or bacteria.

7. An immobilized cell mixture as set forth in claim 1, wherein the immobilizing carrier is an alginate, K-carrageenan, agar, collagen, gelatin, polyacrylamide, a photocrosslinked resin prepolymer or a urethane polymer.

8. An immobilized cell mixture as set forth in claim 1, wherein the aerobic microorganism is fungi, yeast, actinomycetes or bacteria; the anaerobic microorganism is a yeast or bacteria; and the immobilizing carrier is an alginate, K-carrageenan, agar, collagen, gelatin, a polyacrylamide, a photocrosslinked resin prepolymer or a urethane polymer.

9. An immobilized cell mixture as set forth in claim 1, wherein the aerobic microorganism is *Aspergillus awamori* or *Asoergukkys bugerl* the anaerobic microorganism is *Zymomonas mobilus* or *Streptococcus lactis;* and the immobilizing carrier is an alginate or K-carrageenan.

10. A spherical immobilized cell mixture as set forth in claim 1, wherein the diameter of said spherical immobilized cell mixture is about 3 millimeters.

11. A method as set forth in claim 3, wherein culturing said immobilized cell mixtures comprises adding the immobilized cell mixtures to a nutrient medium.

12. A method as set forth in claim 11, wherein the nutrient medium contains an aqueous starch solution.

13. A method as set forth in claim 12, wherein the nutrient medium further contains vitamins or amino acids.

14. A method as set forth in claim 12, wherein the immobilizing carrier further contains vitamins or amino acids.

15. A method as set forth in claim 4, wherein culturing said immobilized cell mixtures further comprises lastly adding said mixture dropwise into an aqueous solution so as to form spherical immobilized cell mixtures.

16. A method as set forth in claim 12, wherein the nutrient medium further contains peptone, yeast extract, $KH_2PO$, $MgSO_4 \cdot 7H_2O$, $FeSO_4 \cdot 7H_2O$ and $CaCl_2$.

17. A method as set forth in claim 12, wherein the nutrient medium further contains yeast extract, trypton, casamino acids, $K_2HPO_4$, $KH_2PO$ and $MgSO_4 \cdot 7H_2O$.

18. A method as set forth in claim 16, wherein the fermentation product is ethyl alcohol.

19. A method as set forth in claim 17, wherein the fermentation product is lactic acid.

* * * * *